United States Patent [19]
Soini et al.

[11] Patent Number: 5,891,738
[45] Date of Patent: Apr. 6, 1999

[54] BIOSPECIFIC MULTIPARAMETER ASSAY METHOD

[75] Inventors: Erkki Soini, Krypingintie 20, FIN-21610 Kirjala; Pekka Hanninen; Juhani Soini, both of Turku, all of Finland

[73] Assignee: Erkki Soini, Kirjala, Finland

[21] Appl. No.: 817,753

[22] PCT Filed: Jan. 3, 1996

[86] PCT No.: PCT/FI96/00004

§ 371 Date: May 13, 1997

§ 102(e) Date: May 13, 1997

[87] PCT Pub. No.: WO96/22531

PCT Pub. Date: Jul. 25, 1996

[30] Foreign Application Priority Data

Jan. 16, 1995 [FI] Finland ................................. 950175
Mar. 7, 1995 [FI] Finland ................................. 951040

[51] Int. Cl.⁶ ..................... G01N 33/533; G01N 33/546; G01N 33/566
[52] U.S. Cl. ................. 436/501; 435/6; 435/7.1; 435/973; 436/523; 436/533; 436/534; 436/800; 436/805
[58] Field of Search .................. 435/6, 7.1, 973; 436/501, 523, 533, 534, 800, 805

[56] References Cited

U.S. PATENT DOCUMENTS

| | | | |
|---|---|---|---|
| 4,421,860 | 12/1983 | Elings et al. | 436/518 |
| 5,028,545 | 7/1991 | Soini | 436/501 |
| 5,034,613 | 7/1991 | Denk et al. | 250/458.1 |
| 5,196,709 | 3/1993 | Berndt et al. | 250/458.1 |
| 5,308,990 | 5/1994 | Takahashi et al. | 250/459.1 |
| 5,518,883 | 5/1996 | Soini | 435/6 |
| 5,523,573 | 6/1996 | Hänninen et al. | 250/459.1 |
| 5,674,698 | 10/1997 | Zarling et al. | 435/7.1 |
| 5,736,410 | 4/1998 | Zarling et al. | 436/172 |
| 5,759,767 | 6/1998 | Lakowicz et al. | 435/4 |

FOREIGN PATENT DOCUMENTS

| | | |
|---|---|---|
| 0 442 025 A1 | 8/1991 | European Pat. Off. |
| 587008 | 3/1994 | European Pat. Off. |
| WO 94/07142 | 3/1994 | WIPO |
| WO 94/11735 | 5/1994 | WIPO |
| WO 94/16313 | 7/1994 | WIPO |

*Primary Examiner*—David Saunders
*Attorney, Agent, or Firm*—Adduci, Mastriani & Schaumberg, L.L.P.

[57] ABSTRACT

The object of this invention is an improved method for biospecific multiparameter assay method based on the use of different categories of microparticles as solid support for different bioaffinity reagents. This invention allows the use of microparticles of small size and with very moderate monodispersity and conventional short decay time fluorescent labels for labelling the biospecific reactants. The high sensitivity of this method is based on the use of confocal excitation and detection, or alternatively, two-photon excitation for measurement of the biospecific reaction. The identification of the category of the microparticle is based on the use of fluorescent or Raman scattering indicators associated with the microparticles representing different analytes.

12 Claims, 7 Drawing Sheets

BIOSPECIFIC MULTIPARAMETER ASSAY METHOD

This invention relates to a biospecific multiparameter assay method. Immunoassays are a well established group of biospecific assays and now widely used in routine diagnostics and research laboratories. Another group of biospecific assays, is DNA hybridization assays. Biospecific assays generally employ one or several biospecific reactants (e.g. antibody, DNA probe) and normally one of these reactants is labelled. The labels currently used are radioisotopic, enzymatic, luminescent and fluorescent labels.

In routine diagnostics there is a growing need for multiparameter (multianalyte) analysis. Unfortunately, the current methodology does not allow the use of more than two or three simultaneous labels because the spectrometric signals from different labels cannot be sufficiently separated. The emission spectra of different radioisotopic labels and photoluminescent labels overlap significantly and as a consequence they provide inadequate separation of different analytes over a required concentration range.

The purpose of this invention is to present a better method for multiparameter biospecific assays. The method according to this invention is based on methods that are generally known within the field of immunology and DNA hybridization. Normally, they are performed as follows. The method uses two biospecific probes that recognize the analyte molecule k. In this text, these probes are referred to as the primary probe $Ab(k,1)$ and the secondary probe $Ab(k,2)$. When the secondary probe is labeled, for example, with a photoluminescent label F, it is denoted with the symbol $Ab^F(k,2)$. In the reaction solution, there is an excess of primary and secondary probes compared to the number of analyte molecules $M_k$. When the analyte molecule, which is either a polypeptide or a macromolecule, has separate epitopes i.e. molecule structures that bind specifically to the probes, they form together a complex $Ab(k,1)+M_k+Ab^F(k,2)$. In principle, the amount of complex formed is directly proportional to the amount of the analyte, and the excess of primary and secondary probes remain in the solution. The complexes are separated from the free probes using a commonly known technique, for example, in which the primary probe is bound to a solid carrier and the free probes are washed away from the sample. Finally, the signal of bound label F in the complexes is measured in a traditional way which depends on the label chosen. The intensity of the signal obtained is directly proportional to the amount of label in the solution, and the response of the system is linear.

If the analyte to be measured is a small molecule without two or more epitopes which specifically bind to the probes, one can use a secondary probe that reacts specifically with the complex formed by the analyte and the primary probe (C. H. Self et al., Clin. Chem. 40 (1994) 2035–2041).

BACKGROUND OF THE INVENTION

Certain multiparameter biospecific assay methods have been introduced earlier. It has been common practice to use multiple labels to label biospecific reagents and to perform the separation of the signals on the basis of their different emission spectra. In most cases, however, the known multiparameter methods are based on the use of a solid support where the biospecific reagents can be immobilized at separate and optically distinguishable areas, or that are based on the use of artificial microparticles as a solid support. Some of the methods are reviewed below:

1. A method, in which various biospecific probes are attached to a matrix, which is formed by small areas on a planar solid support, is described in the patent PCT WO 84/01031. In this method, after the reaction and the wash, the signals from the photoluminescent labels in each area are measured separately, for example, using a laser scanning microscope.

2. A method, in which the identification of the analyte category is based on the color of the microparticles, which are used as a solid support and which is achieved by optically measuring the light absorption of the particle to be analyzed (J. G. Streefkerk et al. Protides Biol. Fluids 24 (1976) 811–814 and U.S. Pat. No. 5,162,863).

3. A method, in which the identification of the analyte category is performed by optically measuring the absorption of the dye inside the particle, the refractive index or the size of the particle to be analyzed (U.S. Pat. No. 5,162,863).

4. A method, in which the identification of the analyte category is based on the use of different particle sizes and in which the identification is performed by optically measuring the diameter of the particle to be analyzed (T. M. McHugh et al., Journal of Immunological Methods 95 (1986) 57–61).

5. A method, in which the microparticles are identified by means of fluorescent dyes that are mixed or impregnated within the particles, and the biospecific signal is measured from the fluorescence intensity of another fluorescent dye, such as FITC (EP 126450, GOIN 33/58).

6. A method, in which a dye emitting short decay time fluorescence (decay time a few nanoseconds), is used for the identification of microparticles, and a dye emitting long decay time fluorescence (decay time from 10 microseconds to 2 milliseconds), is used for measuring the analyte concentrations, and in which a time resolved fluorometer is used for the discrimination of the short and long life time fluorescence (U.S. Pat. No. 5,028,545).

7. A method, in which a dye emitting short decay time fluorescence (decay time a few nanoseconds), is used for the identification of the microparticles, and a molecule which generates chemiluminescence or bioluminescence (decay time several seconds), is used to measure the analyte concentrations, and in which the fluorescence and luminescent signal can effectively be separated from the fluorescence because they are excited and they emit light at different times (FI-patent 89837).

8. A method, in which a dye emitting short decay time fluorescence (decay time a few nanoseconds), is used for the identification of the microparticles and a dye emitting phosphorescence, (decay time from 10 microseconds to 2 milliseconds), is used to measure the analyte concentrations, and in which a time resolved fluorometer is used for the discrimination between the short decay time fluorescence and the long decay time phosphorescence (FI-patent 90695).

9. A method, in which dyes emitting long decay time fluorescence, such as fluorescent chelates of lanthanide ions Tb, Dy, Eu and Sm, are used for the identification of the microparticles and for measurement of the biospecific signal (FI-patent application 931198).

A common problem in many multiparameter assays mentioned above is that the signal of photoluminescent label, which indicates the analyte category, and the signal from the photoluminescent label, which measures the concentration of the biospecific probe, interfere with each other. This is a problem that significantly restricts the dynamic range of the measurement of the analyte concentration. This interference may become particularly significant when measuring low analyte concentrations and when a wide dynamic range is required for the measurement of the biospecific signal. In methods 6, 7, and 8 referred to above, interference is eliminated by choosing such photoluminescent labels for the measurement of the biospecific reaction and identification labels which have substantially different emission decay times. In methods 1, 2, 3 and 4 the analyte is identified using an alternative method rather than using a photoluminescent label. In methods 5 and 9, the identification method of the analyte essentially restricts the dynamic range of the measurement.

Another problem associated with methods 6, 7, 8 and 9 mentioned above is the long measurement time, caused by the long decay time (T½=1 millisecond) of the fluorescent and phosphorescent labels. This problem is caused by the saturation of the excited states of the labels, which restricts the intensity of the exciting light to such a low level that a measurement time of up to one second is needed for each microparticle. Likewise, the measurement of the signals from labels that are based on chemiluminescence, bioluminescence and electroluminescence, also take at least one second.

OBJECTS OF THE INVENTION

The object of this invention is an improved method for biospecific multiparameter assay method based on the use of small microparticles with a diameter range from 100 nanometer to 10 micrometer, but not limited to these measures. The microparticles are used as solid support for different bioaffinity reagents in reaction solution to which the sample is added. This invention allows the use of microparticles with very moderate monodispersity. The method of this invention allows the use of conventional short decay time fluorescent labels for labelling the biospecific reactants. Despite the fluorescent background, which is normally associated with such fluorescent labels, the optical measurement method of this invention ensures an ultimate sensitivity which potentially can be one molecule per microparticle.

The following terms are used systematically later in the text: The term "indicator" is used in the context of a substance used for identification of the microparticles. The term "dye" will be used if the indicator is a fluorescent dye. The term "label" will be used in the context of labelling of the biospecific reactant with a photoluminescent label F, which is a fluorescent dye with short decay time.

In particular this invention relates to the method of sensitive detection of the signal from the label F and identification of the category of microparticles using indicator $D_k$.

DETAILED DESCRIPTION OF THE INVENTION

In the method of this invention, the microparticles are in different categories representing different analytes to be assayed, said categories comprising different amounts of one or several indicators $D_1$, $D_2$, $D_3$, ... $D_k$ (later $D_k$), for the purpose of identification of the category of said microparticles. Each category of microparticles is coated with a different biospecific reactant Ab(k,1), which reacts with the particular analyte $M_k$ and with a secondary reagent $Ab^F(k,2)$ and which is labelled with a photoluminescent label F. Complexes Ab(k,1)+$M_k$+$Ab^F(k,2)$ are formed in the reaction on the surface of the microparticles belonging to category k and the signal from the label F is then measured and used for determination of the concentration of each analyte $M_k$ in the reaction solution.

Said method is comprised of steps of:

pooling the different categories of microparticles coated with the primary reagent Ab(k,1) together in a suspension and adding the sample M containing analytes $M_1$, $M_2$, ... $M_k$ to be assayed into the suspension, adding a mixture of labelled biospecific secondary reactants $Ab^F(k,2)$ into the suspension to initiate biospecific reactions between the analytes $M_k$ and the labelled reactants and microparticle-associated reactants Ab(k, 1), diluting the suspension to reduce the concentration of labelled reactants not bound to the microparticles, sampling the suspension in order to expose one microparticle at a time to a laser beam and exciting the indicators $D_k$ and the photoluminescent label F associated with the microparticle, converting the signal obtained from the excited indicators $D_k$ and from the label F to electrical signals, identifying the category of each microparticle on the basis of the electrical signal resulting from the indicator $D_k$, determining the concentration of the analyte $M_k$ on each microparticle on the basis of the electrical signal resulting from the photon emissions generated by the label F.

A sufficient number of microparticles is analyzed and the result of each microparticle is registered in a computer.

The suspension is diluted adequately after the reaction. Often a dilution of one order of magnitude may be enough for sufficient separation of the bound and free fraction, because the photometric detector used in this invention is able to discriminate optically between those signals originating from the microparticle within the optical focal volume and the signal from the free label in the surrounding buffer solutions.

The photoluminescent label F in the method of this invention, is a short decay fluorescent compound and the sample is illuminated by a continuous or pulsed laser beam which excites the fluorescence emissions. The fluorescent label, with a typical emission decay time of a few nanoseconds, allows one to use an intensity of the exciting light up to $10^6$ times higher than that of the excitation intensity of the long decay time fluorescent labels in the method referred to above. A much stronger signal with a short decay time can be derived from labels and, correspondingly, the signal can be measured precisely in much shorter time. Since the time needed for detecting one microparticle is very short, for example 100 microseconds, the method of this invention has the advantage that a large number of microparticles can be measured within a short time. This results in higher capacity, accuracy and precision.

The background signal, which seriously reduces the sensitivity of ordinary fluorometry, is eliminated in this invention by using confocal excitation and detection or alternatively, by using two-photon excitation. Both of these methods restrict the active volume of measurement to a diffraction limited volume which approximately corresponds to the volume of one microparticle. Both of these methods and the related optical systems discriminate very efficiently all background scattering and fluorescence which originate from outside the active diffraction limited sample volume.

It is essential for the sensitivity of the method of this invention, as well as for the sensitivity of the other multi-parameter assays previously known and referred to above, that the signal from the indicator used for the identification of the analyte, does not interfere with the signal from the photoluminescent label used for the measurement of the biospecific reaction. In this invention, this interference has been eliminated by using identification with nonfluorescent indicators or alternatively, when using a fluorescent indicator, the interference is eliminated with the use of the two-photon excitation method.

Realization of the Invention with the Confocal Principle

Figure 1:
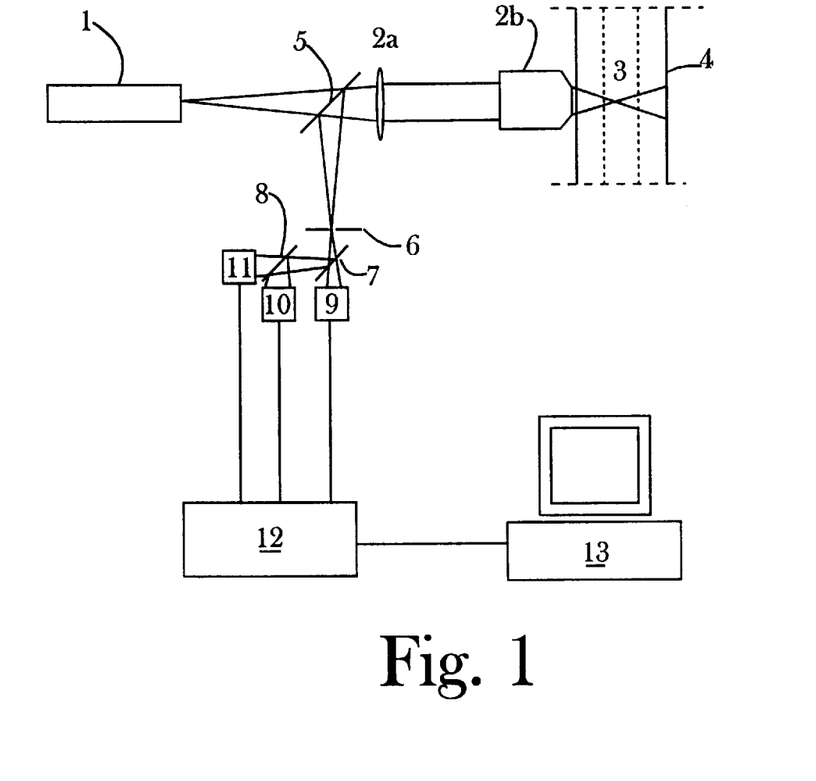
FIG. 1 is a functional diagram of the measuring system needed for the method of this invention.
Figure 2A:
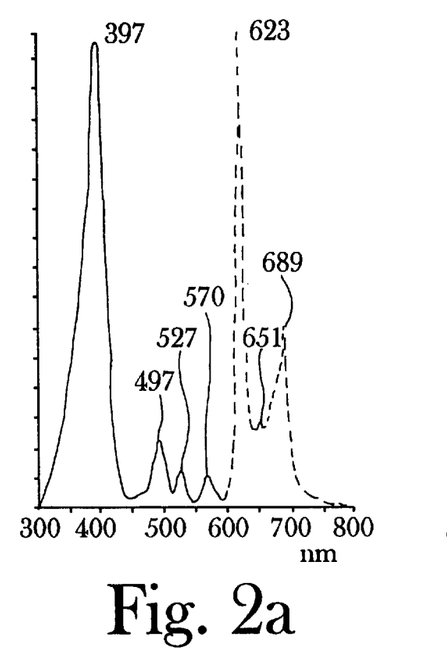
FIGS. 2a–2j show the excitation and emission spectra of the tetrapyrrolic compounds, which can be used as indicator $D_k$.
Figure 2B:
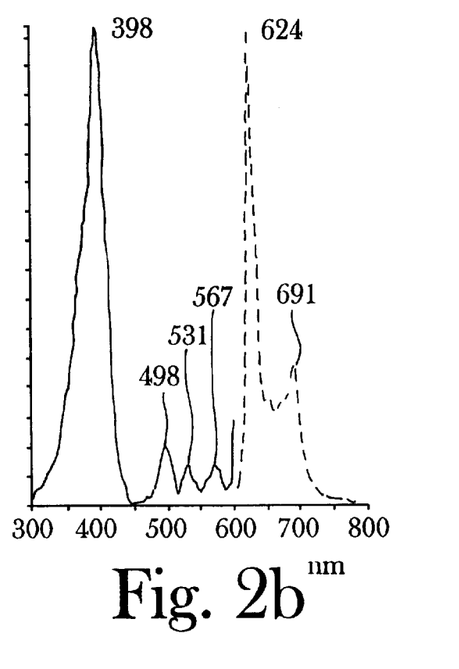
Figure 2C:
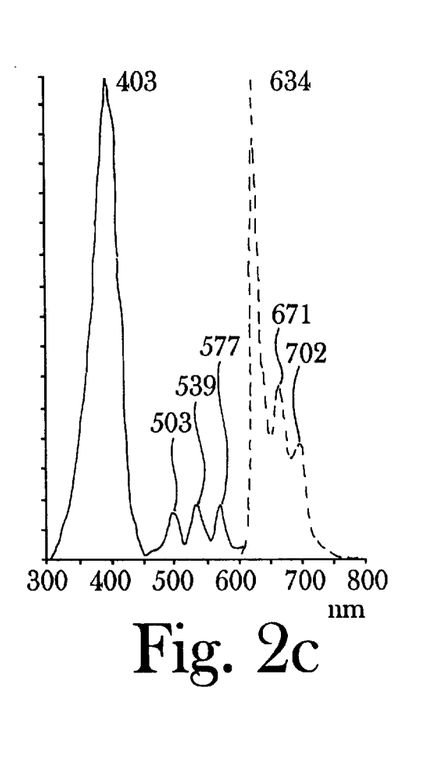
Figure 2D:
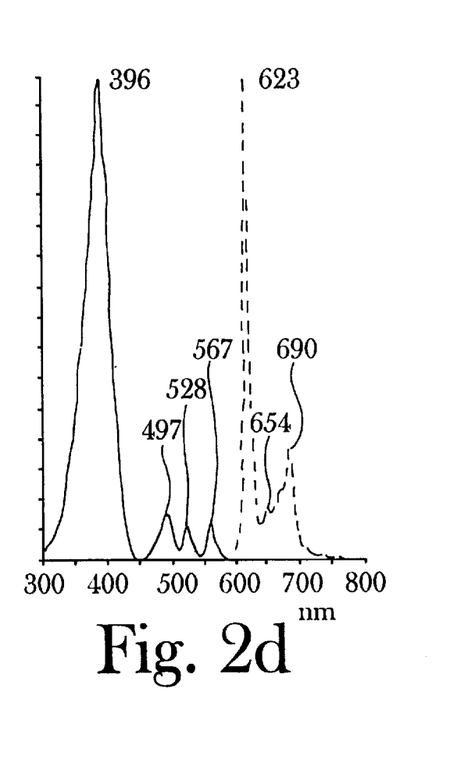
Figure 2E:
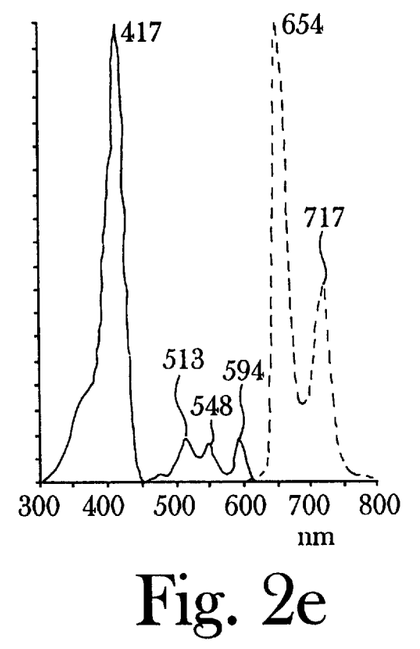
Figure 2F:
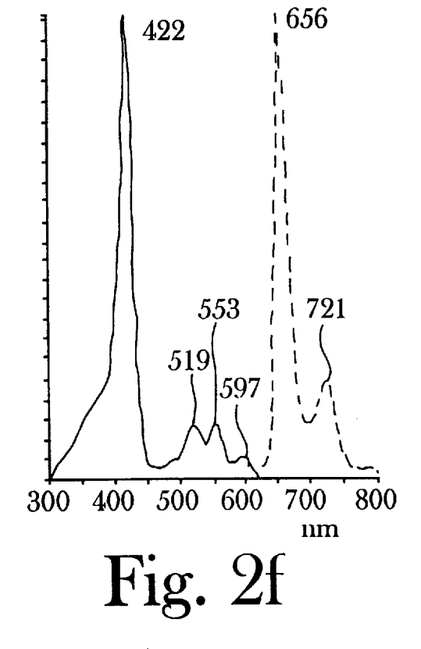
Figure 2G:
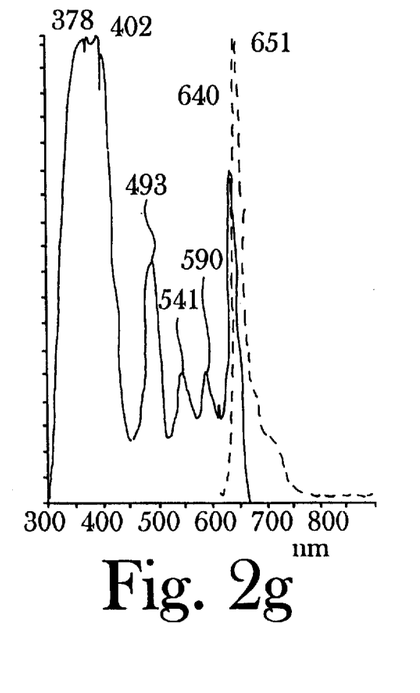
Figure 2H:
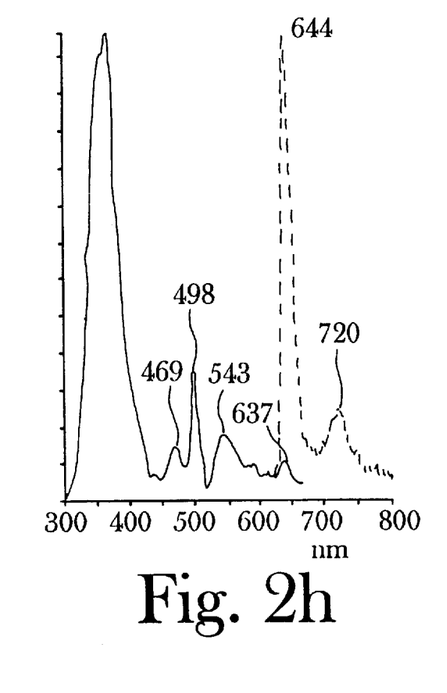
Figure 2I:
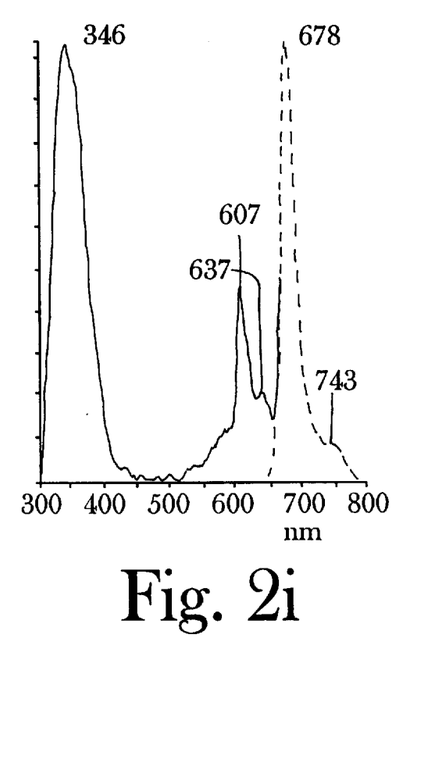
Figure 2J:
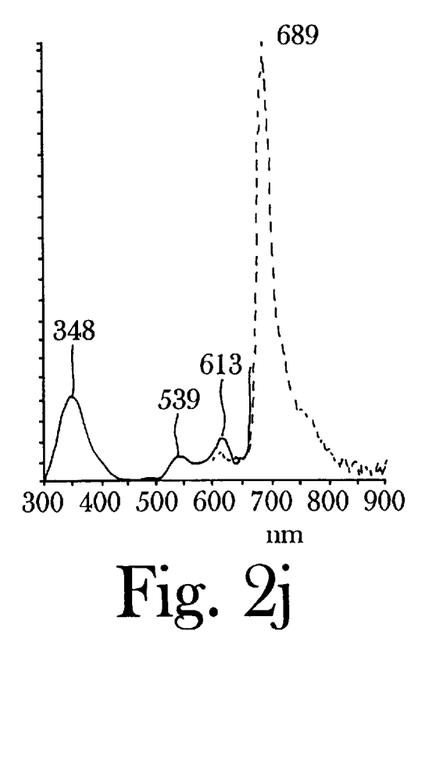

The confocal principle applied to this invention is described in following with the reference to FIG. 1, which shows an example of the functional diagram of the measuring system needed for the method of this invention. The laser (1) is used for excitation of fluorescence and it is focused through a lens (2a) and an objective lens (2b) to the sample (3) in a capillary cuvette (4). The fluorescence signal from the sample is directed by a dichoic mirror (5) to a pinhole (6). The light beam from the pinhole (6) is spit by dichroic mirrors (7) and (8) passes to the detectors (9), (10) and (11), which are tuned for the wavelengths of label F and indicators $D_1$ and $D_2$ respectively. For simplicity, the functional diagram presented now is applied to the registration of only two spectral features of the indicators $D_k$ requiring two detectors (10) and (11), respectively. The detectors incorporate appropriate spectral filters. The detectors (9), (10) and (11) are connected to a signal processor (12). The signal processor converts the signals to numerical form and the results are processed in the computer (13), which also controls the hardware. The label F and the indicator $D_k$ can also be excited with different lasers, if their excitation wavelengths are different, or if better results can be achieved by using two lasers. In this case, both lasers are focused to the same or adjacent points of the moving sample.

The principle of the confocal set-up is described below with reference to FIG.1. Firstly, imaging of a point-like light source (1) to the focal plane (3) of the objective lens (2b) is described. Due to diffraction, a point-like source of light forms an intensity distribution, which is characteristic to the optical system, in the focal plane. The intensity distribution is called the point spread function, which is determined in three dimensions. A normalized point spread function defines the probability S1 of how photons, radiated from a point-like source, are distributed on the focal area (3); that is, the probability that the photons are absorbed to different parts of the sample volume.

A corresponding point spread function S2 can also be determined for the spatial distribution of the photons emitted from the focal point that reach the pinhole in front of the detectors. The value of this normalized function in the vicinity of the focal point defines the probability of the photons emitted from different points and hitting the pinhole (6).

In the confocal optical system that has been applied to the method and the device of this invention, the light source (1) and the pinhole (6) are focused to the same focal point (3). The probability that a photon radiated from a point-like light source (1) causes a fluorescence emission in the sample, and that the emitted photon hits the pinhole (6), is described by the normalized product S1*S2 of the illumination and detection intensity distributions. The probability distribution thus derived, is three dimensional and is clearly more restricted than the one produced by conventional optics, especially in the axial direction. The fluid volume to be measured in a confocal system is considerably smaller than the one in a conventional optical system. When using an objective lens with a large numerical aperture (N.A.>0.5) and a confocal system, the active fluid volume is reduced to under a tenth of what is required in a conventional optical system. The dimension of the fluid volume under observation, is clearly larger axially than laterally, and it is inversely proportional to the square of the numerical aperture (N.A.).

Realization of the Invention with two Photon Excitation

An alternative labelling and detection method that allows the use of fluorescent dyes as the identification indicator $D_k$ and offers a good separation between the signals from $D_k$ and F, is based on two-photon excitation of the label F.

Normally, the fluorescent labels are single-photon excited, which means that the chromophores of the fluorescent label absorb light at the wavelength of the exciting light beam. Two-photon excitation can replace single-photon excitation and reduce the background caused by scattering and autofluorescence and it also very efficiently eliminates the spectral interference between $D_k$ and F. Two-photon excitation is possible when, by focusing an intensive light source, the density of photons per unit volume and per unit time becomes high enough for two photons to be absorbed into the same chromophore. In this case, the absorbed energy is the sum of the energies of the two photons. Already in the 1930's, two-photon excitation of fluorescent materials was theoretically known, and from the 1960's on it has been applied in the fields of spectroscopy and microscopy (U.S. Pat. No. 5,034,613). According to the concepts of probability, the absorption of a single photon by a chromophore, is an independent event, and the absorption of several photons is a series of single, independent events. The probability of absorption of a single photon can be described as a linear function as long as the energy states that are to be excited are not saturated. The absorption of two photons is a non-linear process of the second kind. In two-photon excitation, the chromophore is excited only when both photons are absorbed simultaneously, which is approximately within a femtosecond. The probability of absorption of two photons is equal to the product of probability distributions of absorption of the single photons. The intensity of fluorescence emission, caused by two photons, is thus a quadratic process with respect to the photon density of illumination.

The properties of this invention's optical system have been described above with respect to the response of the system to a point-like light source. A point-like light source forms, due to diffraction, an intensity distribution in the focal plane characteristic of the optical system (point spread function). When normalized, this point spread function is the probability distribution for the photons from the light source to reach the focal area. In two-photon excitation, the probability distribution of excitation equals the normalized product of the intensity distributions of the two photons. The probability distribution thus derived is 3-dimensional, and is clearly more restricted than that for single-photon excitation, especially in the vertical direction. Thus in two-photon excitation, only the fluorescence that is formed in the clearly restricted 3-dimensional vicinity of the focal point is excited.

When a chromophore is two-photon excited and the excitation is restricted to the 3-dimensional vicinity of the focal point, then the signal caused by scattering in the vicinity of the focal point and from the optical components, is reduced remarkably if compared to normal excitation. Furthermore, two-photon excitation decreases the background fluorescence outside the focal point, in the surroundings of the sample and in the optics. Since the exciting light beam must be focused onto as small a point as possible, two-photon excitation best suits the observation of small sample volumes and structures, which is also the situation in the method according to this invention.

The previously mentioned advantages of two-photon excitation are based on the fact that visible or near-infrared (NIR) light can be used for excitation in the ultraviolet or blue region. Similarly, excitation in the visible region can be achieved by NIR light. Because the wavelength of the light source is considerably longer than the emission wavelength of the chromophore, the scattering at a wavelength of the light source and the possible autofluorescence can be effectively attenuated by using low-pass filters (attenuation of at least 10 orders of magnitude) to prevent them from reaching the detector.

The common way to produce two-photon excitation is to use ultra-short laser pulses. During the short pulse, it is possible to achieve a sufficiently high energy density for two-photon excitation, but the average energy is kept low. It has been observed, though, that two-photon excitations can also be observed with continuous-wave laser illumination.

In our experiments, we have observed that a very high signal-to-background-ratio and good sensitivity can be reached with two-photon excitation and short-lived fluorescent labels. Suitable fluorescent labels for two-photon excitation are, for example, coumarin, rhodamine derivatives and phycobiliproteins.

In using the method of two-photon excitation, the coincidence condition of the laser pulse and the pulse from the photon detector can also be used to eliminate thermal noise from the photon detector. In this case, thermal noise becomes insignificant. The use of two photon excitation is advantageous compared to any single-photon excitation method because scattering and background noise, especially that caused by proteins and other macromolecules in the sample, is considerably lower. No fluorescence arises at the wavelength of the laser, nor can scattering caused by the laser beam reach the detector, because low-pass filters effectively block wavelengths lower than that of the laser.

Two-photon excitation can best be performed with pulse lasers. The short transit time requires a pulsed laser with very high repetition frequency. Today, the laser suitable for this application is the titanium-sapphire femtosecond laser with pulse energy of 10 nJ and with pulse frequency of 76 MHz and with adjustable 700–900 nm wavelength. Less expensive pulsed lasers suitable for this application will likely be available in the near future. An example of this kind of development is the mode-locked 300 MHz pulsed diode laser (Laser Ionics Inc., Orlando, Fla., USA), lambda=825 nm, pulse energy 0,03 nJ, pulse width 1–20 ps. Another example is a new, not yet commercially available diode pumped CrLi-Sapphire laser with 80 MHz pulse rate, 30 fs pulse width, 0.5 nJ pulse energy and adjustable 820–900 nm wavelength.

Two-photon excitation can provide a diffraction-limited focal volume which is slightly larger than that of the confocal set-up, but clearly defined in three dimensions. The lower resolution is simply a consequence of using a longer excitation wavelength for two-photon excitation. However, the optical system for two-photon excitation can also be combined with a confocal set-up. By choosing an appropriate detector pinhole it is possible to optimize the size of the focal volume.

Identification of the Microparticles with Raman Indicators

The use of Raman indicators is an alternative method for identification of the microparticle category. This method is well suited both for the confocal and two-photon excitation concept.

Raman scattering is inelastic light scattering from molecular structures where the energy due to molecular vibrations is mixed with the Raman scattering due to light excitation. The Raman spectrum is expressed as a wavelength shift on both sides of the wavelength of the incident light, and called the Stokes shift and the anti-Stokes shift. A Raman spectrum includes information from the molecular structure similar to that from an infrared (IR) spectrum. Raman spectrum can also be obtained from very small objects like microparticles (P. Dhamelincourt & al. Spectroscopy Europe 5/2(1993) 16–26). Therefore, Raman spectra can be used to identify and to distinguish different molecular structures of microparticles.

Microparticles for different categories can be produced with known polymerization methods employing chemically different monomer mixtures for different particle categories. The monomer mixtures can include different kinds of monomers in different quantities or indicator substances can be added to the monomer. Examples of different monomers suitable for polymerisation and having significantly different Raman spectra are styrene, deutered styrene (=styrene-D6), methylmethacrylate and acrylonitrile. Examples of additional indicators are oligomers or polymers of above mentioned monomers or aliphatic or aromatic halogen compounds.

Microparticles with a diameter ranging from 100 nanometers to 10 micrometers can be produced from different materials or material composites. The microparticle indicator substances can be added to production batches of different categories of microparticles and in different combinations. Thus the Raman signals from different indicators express the category to which the microparticle belongs. For example, when using styrene as main component of the monomer mixture for particle synthesis and when using the other three monomers mentioned above, as indicators, it is possible to produce microparticles in $2^3=8$ different categories. The Raman spectra obtained from microparticles of these different categories can be recognized by comparing the spectra using the correlation method described e.g. in U.S. Pat. No. 5,313,406 or by comparing the intensities of certain individual spectral peaks.

Identification of Microparticles with Fluorescent Indicators

The use of fluorescent dyes is an alternative method for identification of a microparticle's category. This method is well suited only for the two-photon excitation concept because spectral overlap may cause significant interference in the confocal concept.

Fluorescent microparticles with a diameter ranging from 100 manometers to 10 micrometers can be manufactured combining the polymer material with a suitable short decay time fluorescent dye. Well known fluorescent dyes with very short decay time, for example POPOP, bisMSB, fluorescein or rhodamine etc., can be added to any monomer (as discussed e.g. in "Theory and Practice of Scintillation Counting", Ed. J. B. Birks, Pergamon Press, 1967, pp. 321–353) and solid fluorescent material is formed in polymerization. The material can be processed into microparticles in the same step. The fluorescent dyes can alternatively be impregnated into the surface of the microparticles or coupled on the surface of the microparticles. The fluorescent dye can be added into different batches of the monomer in substantially different concentrations differing e.g. by a factor of two from each other.

Irrespective of the choice of the label F and excitation method, several compounds with short fluorescence decay time can be used as an identification dye $D_k$. It is clear that the measuring device needed in this method can be simplified, if the excitation wavelength for all of the chromophores, F and $D_k$, is the same, and the emission wavelengths differ substantially from each other, so that they can easily be separated spectrally. It is important that the fluorescent dye chosen has an absorption band that does not overlap with the emission band of the photoluminescent label F. The measuring device is simplified, if the chromophores F and $D_k$ can both be excited with the same light source.

In case of two-photon excitation, for example, each of the chromophores, F and $D_k$, can be two-photon excited, or alternatively, F is two-photon excited and the fluorescent dyes of the NIR region are used as chromophores $D_k$ and they are one-photon excited by the fundamental wavelength of the same laser. However, if chromophores similar to the ones described above are not used, it is necessary to excite them with two separate lasers, which are focused to the same or adjacent points of the moving sample. The excitation of the points, and the emission that follows it, are separated in the time domain.

The potential fluorescent chromophores $D_k$ should show the following properties. In the method according to this invention: 1) They must have a common fluorescence excitation wavelength, which lies, if possible, on the excitation range of the bioaffinity label F, or at the fundamental wavelength of the laser that is used for the two-photon excitation of F; 2) they must have spectrally separable fluorescence emission bands that are higher than that of F; 3) the decay time of their fluorescence excited states must be short, and lie in the nanosecond range; in addition it is advantageous for a good function of this invention if 4) they have a large difference between their excitation and emission wavelengths; 5) they have no significant long decay emission component; 6) they are chemically stable and attachable to the microparticles; and 7) it would be very useful if their susceptibility to two-photon excitation is lower than that of F.

The following commercially available and widely used dyes meet these specifications: Hoechst 33258, rhodamine (TRITC), Texas Red and Quantum Red. Although the excitation maxima of these dyes lie at different wavelengths, they can still be reasonably well excited at a single wavelength in the 300 to 450 nm range. The emission maxima lie at wavelengths of 470, 570, 620 and 670 nm, respectively.

A group of compounds suitable for dyes $D_k$ can be found among the following group of tetrapyrrols: porphyrins, chlorines, bacteriochlorines, purpurines, pheophorbides, phthalocyanines and naphthalocyanines. These compounds generally have overlapping absorption bands at a near-UV range (320 nm–450 nm, the so called "Sores band") but also from the visible to the NIR-range and narrow separate fluorescence emission bands at the red and NIR-range (600 nm–1200 nm). These compounds can be produced synthetically or microbiologically (Porphyrins, D. Dolphin, Ed., Elsevier Amsterdam-N.-Y.-London, 1980, V. 1–3) and they have been used in various analytical applications (D. B. Papkovsky, Appl. Fluor. Technology 3 (1991) 16–23; EP 0127797; EP 0071991; Russian patent SU 1,659,477). Examples of tetrapyrrolic dyes are: 1) deuteroporphyrine IX, 2) mesoporphyrine IX, 3) proto-porphyrine (IX) dimethyl ester, 4) octaethylporphin, 5) tetraphenylporphin, 6) tetra-(2-metoxy)-phenyl-porphin, 7) chlorine of coproporphyrin dimethyl ester, 8) bacteriochlorine of coproporphyrin dimethyl ester, 9) aluminium phthalocyanine and 10) zinc phthalocyanine.

Another group of compounds suitable for dyes "D" can be found among the cyanine dyes. Examples of such cyanine dyes are:

3.3'-diethylthiatricarbocyanine perchlorate,
1.1'-diethyl-2.2'-dicarbocyanine iodide,
3.3'-diethyloxadicarbocyanine iodide,
3.3'-diethyloxatricarbocyanine iodide,
3.3'-diethylthiadicarbocyanine iodide,
3.3'-diethylthiatricarbocyanine iodide.

TABLE 1

| Dye | $\lambda$exc | | | | | | $\lambda$em | | |
| --- | --- | --- | --- | --- | --- | --- | --- | --- | --- |
| 1 deuteroporphyrin IX | 397 | 496 | 527 | 569 | | | 622 | 651 | 689 |
| 2 mesoporphyrin IX | 398 | 498 | 531 | 569 | | | 624 | 691 | |
| 3 protoporphyrin IX, dimethylester | 402 | 503 | 538 | 516 | | | 633 | 671 | 702 |
| 4 octaethylporphin | 392 | 496 | 527 | 567 | | | 623 | 653 | 689 |
| 5 tetraphenylporphin | 416 | 512 | 548 | 593 | | | 654 | 717 | |
| 6 tetra-(o-methoxy)-phenylporphin | 421 | 518 | 552 | 597 | | | 656 | 721 | |
| 7 chlorin of coproporphyrin dimethyl ester | 377 | 402 | 492 | 541 | 590 | 640 | 650 | | |
| 8 bacteriochlorin of coproporphyrin dimethylester | 370 | 468 | 498 | 542 | 636 | | 643 | 720 | |
| 9 aluminium phthalocyanine | 345 | 607 | 636 | | | | 679 | 748 | |
| 10 zinc phthalocyanine | 347 | 538 | 612 | | | | 689 | | |
| 11 3.3'-diethylthiatricarbocyanine perchlorate | 772 | | | | | | 818 | | |
| 12 1.1'-diethyl-2.2'-dicarbocyanine iodide | | | | | | | | | |
| 13 3.3'-diethyloxadicarbocyanine iodide | 578 | | | | | | 605 | | |
| 14 3.3'-diethyloxatricarbocyanine iodide | 695 | | | | | | 719 | | |
| 15 3.3'-diethylthiadicarbocyanine iodide | 662 | | | | | | 679 | | |
| 16 3.3'-diethylthiatricarbocyanine iodide | 772 | | | | | | 820 | | |
| 17 IR-125 | 795 | | | | | | 833 | | |
| 18 IR-132 | 832 | | | | | | 905 | | |
| 19 IR-140 | 826 | | | | | | 882 | | |
| 20 IR-144 | 745 | | | | | | 825 | | |
| 21 coumarin 120 | 334 | 393 | | | | | 426 | | |

Additional examples are commercial laser dyes such as IR-125, IR-132, IR-140 and IR-144 (Eastman Laboratory Chemicals, Catalog No. 55, Edition 93–94)

The excitation (exc) and emission (em) wavelengths of the tetrapyrrolic and cyanines dyes listed above are presented in Table 1. The excitation and emission spectra of the compounds 1–10 are shown in FIG. 2a–2j. It can be seen that the spectra fulfil the requirements 1–4. Regarding requirement 6, we have found that tetrapyrrolic dyes show very low susceptibility to two-photon excitation. Phycoerythrin, for example, shows very high susceptibility to two photon excitation. Because of this feature, tetrapyrrol dyes and phycoerythrin are a very good combination as $D_k$ and F.

These tetrapyrrolic and cyanine dyes can be supplemented with other known organic fluorescent dyes having the same excitation wavelength and showing an emission band either within the lower or the higher side of the emission range of tetrapyrrolic or cyanine dyes. An example of this kind of compound is coumarin 120 in Table 1.

Figure 3A:
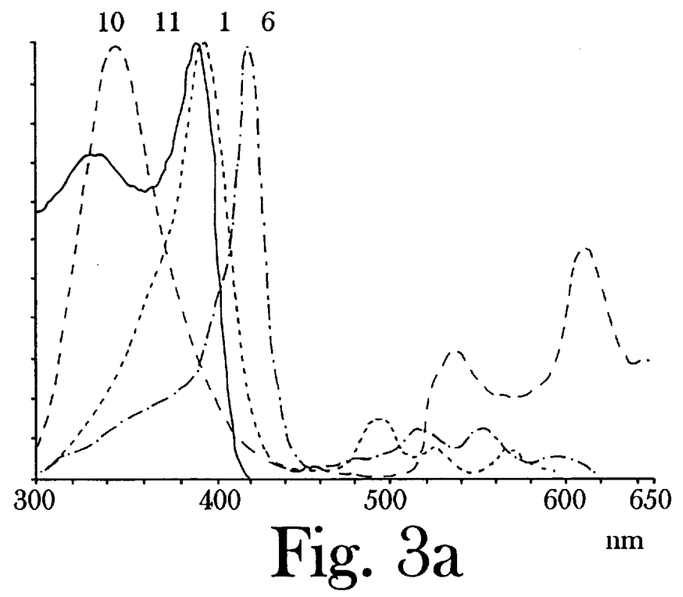
FIGS. 3a and 3b show the excitation and emission spectra of selected tetrapyrrolic compounds which can be used as indicator $D_k$.
Figure 3B:
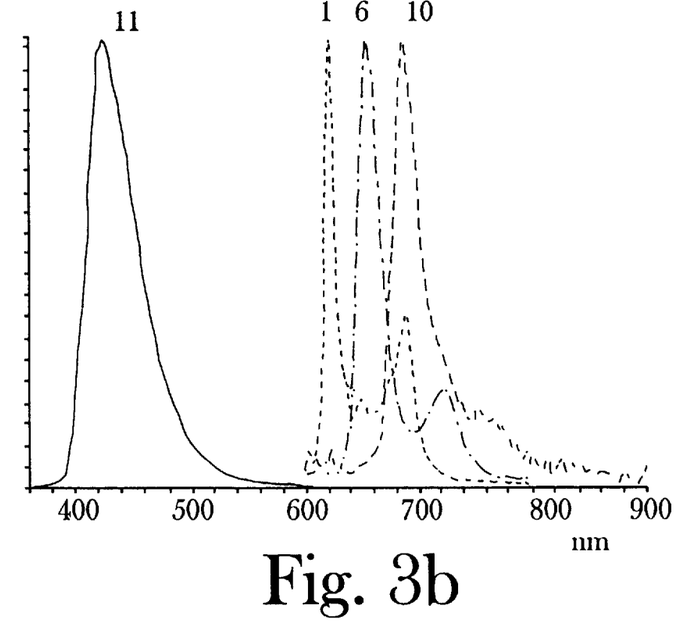

It can be seen from the excitation and emission spectra of the tetrapyrrolic compounds 1–10 presented in FIG. 2a–2j that it is easy to find at least three different compounds with separate emission spectra. As an example we show in FIG. 3b emission spectra for three compounds 1, 6 and 10, their emission wavelengths being 623 nm, 656 nm and 689 nm, respectively. These compounds are shown together with the emission spectrum of coumarin. The spectrum for each compound can be measured over a minimum of one order of magnitude dynamic range without any significant interference by the other compounds when the concentrations of the other compounds vary to same degree. The excitation spectra of these same compounds are presented in FIG.3a. All compound can be excited in the wave length range of 350–400 nm. The compounds were in a solid matrix (Merckoglas). In FIG. 3b the excitation spectrum (solid line) and the emission spectrum (dotted line) are shown.

Microparticles having fluorescent dyes like tetrapyrrolic or cyanine dyes, either internally or on their surface, can be produced by different known methods. The dyes can be attached to the particle surface covalently if the particles are provided with chemically active groups (Molday, R. S. et al., J. Cell. Biol., 64 (1975) 75–88). The dye can also be impregnated within the surface layer of the microparticles by swelling the particles first in an organic solvent and then by washing and evaporating the solvent after impregnation. These methods have been described e.g. in following manufacturer's publications: Dyeing Large Particles, published by The Dow Chemical Co., 1972 and Uniform Latex Particles, published by Seragen Diagnostics Inc. Naturally the dyes can be added to the raw material before polymerization of the particle.

Signal Analysis

Figure 4:
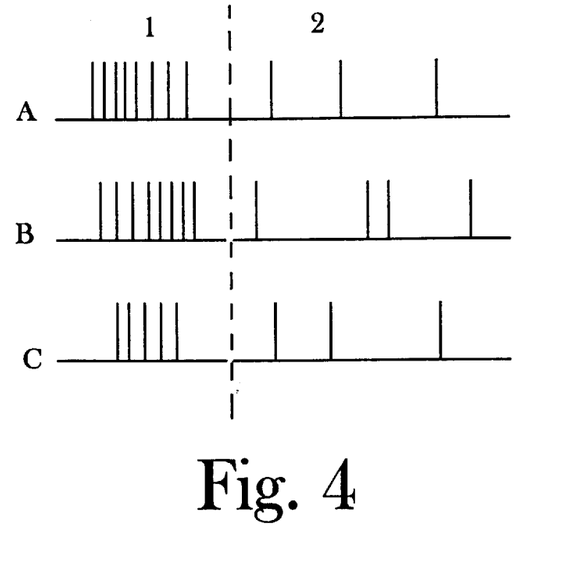
FIG. 4 presents an example of signals derived from the detector.

One possible design concept is to use single photon counters as detectors (9) (10) and (11) in FIG. 1. The signals from these detectors are characteristically single photon signals, which are transformed to binary digital signals with a duration, for example, of 10 nanoseconds. FIG.4(A), 4(B) and 4(C) present examples of pulses derived from the detectors as a function of time. A microparticle remains for a time $t_m$, referred to as transit time, under the excitation of the laser beam within the volume defined by the point spread function of the confocal optics. In practice, the transit time depends on the speed of the flow inside the cuvette (3, FIG. 1), and is typically 100 microseconds. The intensity of the laser beam, used for excitation of label F, can be set so high at the focal point (3) that it can nearly saturate the excited states. If the decay time of the fluorescent labels F is only about 1 nanosecond, the particles can be excited and relaxed up to $10^5$ times within the time interval of $t_m=100$ microseconds under the influence of a powerful laser beam. The number of photons observed by the detector, depends on the quantum efficiency of the label F, the collection efficiency and the losses due to the optics and the quantum efficiency of the photon detector (9). In practice, a detection efficiency of $10^{-2}$ can be obtained using avalanche photon diode counters with 80% quantum efficiency (EG&G Optoelectronics, Canada, type SPCM-141-AQ). Within the transit time $t_m$, the detector (9) can detect one or many photons from the fluorescence emission which come from one microparticle flowing through the active volume. The photons appear as stochastic photon bursts within the transit time $t_m$ (section 1, FIG.4). In addition to these bursts, many other stochastic signals may also be detected (section 2, FIG.4). They originate from the background fluorescence, from free molecules in the sample and from scattering and thermal noise.

An alternative photon detector is a photomultiplier tube and in particular a hybrid photomultiplier tube, which is composed of a single stage electron multiplier and a silicon diode as the electron sensor. This photomultiplier tube is capable of producing an analogue pulse which resolves a single photon. The advantage of the photomultiplier tube is its high dynamic range but the disadvantage is a quantum efficiency one order of magnitude lower than that of avalanche photo diodes. It is useful to adjust the laser intensity to the optimal frequency of single photons to be detected during the photon burst from each kind of sample to be analyzed. If the laser intensity is too high, the rate of photons exceeds the counting speed of the detector and the Poisson distribution of the counts in the time domain will be distorted and consequently the discrimination between true signal and noise is not optimal when using auto-correlation analysis. The excitation power is an adjustable parameter for the optimal photon emission rate from the samples in each particular application.

The avalanche diode photon counter may generate spontaneous after-pulsing with the probability of $10^{-3}$. Avalanche photon counters, as well as photomultiplier tubes, suffer from thermal noise which appears as stochastic counts. The afterpulsing and the noise can be eliminated with the following alternative methods. Auto-correlating the signals form avalanche photon counters with a threshold of 3 counts or higher eliminates the background caused by after-pulsing, but this is made at the cost of detection efficiency. By dividing the emission beam into two parts with a 50%/50% beam splitter for two separate photon counters and using a cross-correlator, it is possible to discriminate the afterpulses and thermal noise. The increased optical losses can be compensated with increased laser power.

The discrimination power between the background counts and the true counts from the particles can be enhanced further by cross-correlating the signals obtained from detectors (9), (10) and (11).

The correlation analysis of the single photon counts can include both auto-correlation analysis and cross-correlation analysis. The auto-correlation analysis is based on registration of the time intervals between the photon counts from each detector. Application of the correlation analysis for two or several independent photon detectors is called cross-correlation. The emitted photons from the true particles, detected by one or several detectors during the transit time of the particle, can correlate in the time domain and within the following correlation parameters: correlation time, correlation thresholds as a minimum number of counts per detector, coincidence threshold defined for the condition of coincident counts from independent detectors. These correlation parameters are adjustable for optimal discrimination of non-specific photon counts.

The device (12) in FIG. 1 performing the correlation analysis for single photon bursts can be an electronic logic circuit, which gives an output signal if a pre-set number of single photon counts from each detector arrives within a pre-set period of time. The circuit may also perform more complex correlation functions or the circuit may be replaced by special computing software which is loaded into a dedicated signal processor or onto a conventional computer.

Throughout, it has been assumed that, depending on the flow speed, the transit time of a microparticle is 100 microseconds. Since the microparticles arrive randomly to the laser beam, and because a combination of two particles or more is not allowed, the counting frequency of the microparticles can at most be 1000 microparticles/s. If, for example, 10000 microparticles of each kind are to be counted and if there are 10 different kinds, then altogether it would take 100 s to measure one sample.

Examples of Performance and Embodiment of the Invention

Example 1

The set-up shown in FIG. 1 was tested in single-photon excitation confocal fluorescence mode with a test-sample of Rhodamine-B dissolved in water in a predetermined concentration. A continuous wave frequency doubled Nd:YAG laser producing 532 nm wavelength was used as a light source. The illumination light was focused to the sample (3) with a microscope objective (2b) with numerical aperture of 0.7. The sample (3) was placed in a position adjustable capillary tube (4) in conjunction with a simple liquid handling system. The emitted fluorescence light was separated from the illumination light by a dichroic filter (5) and a pinhole (6), and detected by a photomultiplier tube (9). The limit of detection was 50 molecules in the focal volume. The sensitivity was limited mainly by the background fluorescence and scattering from the optical components. The dynamic range of the confocal measurement was estimated to be about 3–4 orders of magnitude—the upper end was limited by the maximum concentration of the dye before self-quenching in the sample becomes significant.

Example 2

Figure 5:
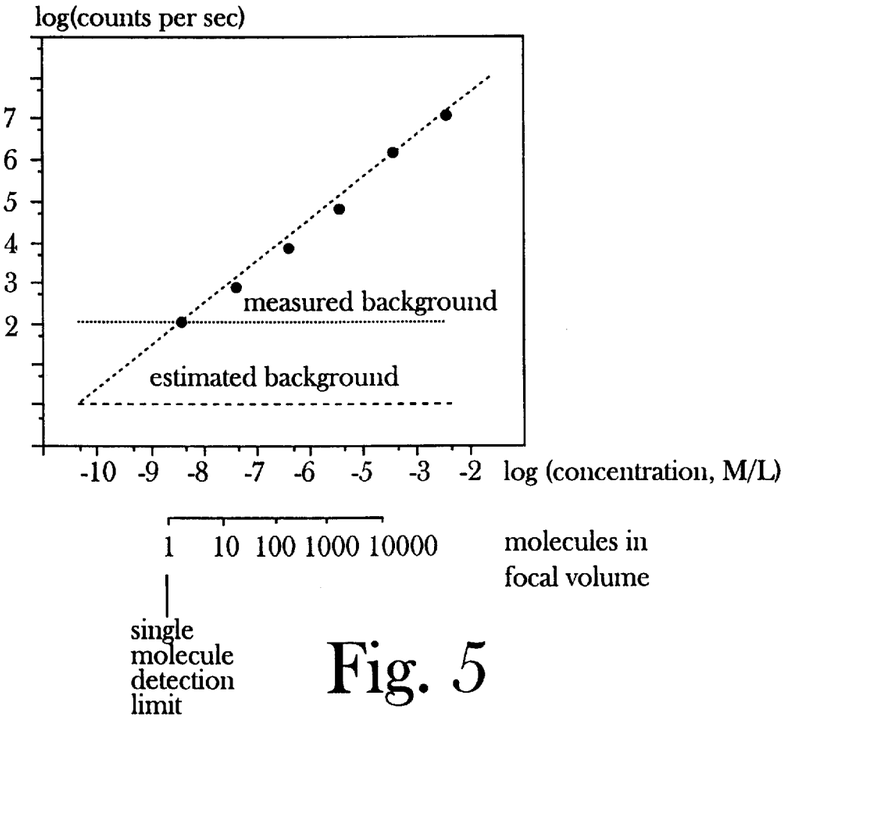
FIG. 5 shows the single photon count rate as a function of the number of molecules in the detector focal volume.

The measurement was performed in two-photon excitation mode with a Q-switched (pulsed) Nd:YAG laser operating at 1064 nm wavelength and 20 kHz repeat rate. In this test the photo-detector dark current was a significant source of background noise but a cross-correlation circuit reduced this background by a factor of 100. The rest of background was caused by second harmonic generation of 532 nm photons at the focal point, but this was suppressed using appropriate filters. The limit of detection was 1 molecule in the focal volume without cross-correlation and without second harmonic suppression filters. In two-photon excitation self-quenching does not play any role. The dynamic range of this test instrument was 5 orders of magnitude and was estimated to be better than 8 orders of magnitude with proper filtering and the cross-correlation system. The results are shown in FIG. 5 which shows the single photon count rate as a function of number of molecules in the focal volume.

As it has become clear from these test measurements, it is feasible to detect single molecules tagged to the microparticles. On a 1 $\mu$m microparticle it is possible to attach $10^6$ antibodies. If 10% are active, the dynamic range of the assay could be $10^5$ even when only a single particle is used as a representative for a particular analyte.

The method and related device is subject to a statistical measurement error which may be significant if the test result is based on only one microparticle. The imprecision is caused by the following factors, for example: the microparticles have a limited monodispersity, the liquid handling system does not provide precise hydrodynamic focusing, the count rate from one microparticle is very limited at lowest concentrations of the analyte. For the purpose of improving the statistical precision of the method it is necessary to measure a large number of microparticles representing different analytes. As it has been discussed above in this text, averaging the results from 1000 or 10000 microparticles ensures sufficient precision in a reasonable time.

As described above, identification of the category can be made using fluorescent indicators $D_k$. It also important that the signal from these indicators does not interfere with the signal obtained from the label F. Spectral filtering does not ensure sufficient separation of the signals obtained from F and $D_k$. This is particularly true if the fluorescence emission spectra overlap and the signals cover a large dynamic intensity range. For reducing these problems we introduce examples of optical set-ups which ensure sufficient separation.

Example 3

Figure 6:
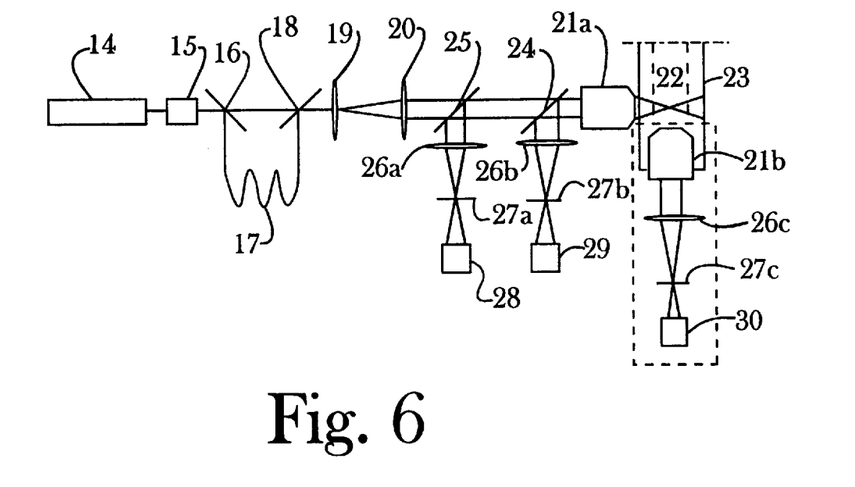
FIG. 6 shows a functional diagram of an alternative measuring system.

With reference to FIG. 6, we assume the use of e.g. phycoerythrin as fluorescent label and a set of tetrapyrrolic dyes as identification indicators $D_k$. This concept provides very good separation of signals because, according to our experiments, tetrapyrrolic dyes show very low susceptibility to two-photon excitation. Phycoerythrin, however, shows very high susceptibility to two photon excitation. Therefore the idea of this example is to use two photon excitation at 1064 nm for phycoerythrin and single photon excitation at 532 nm for tetrapyrrolic dyes. In the instrumental set-up applicable to this example, the fundamental 1064 nm beam from a pulsed Q-switched Nd:YAG laser (14) is frequency doubled in a crystal (15). The 1064 nm and the frequency doubled 532 nm wavelength within the same beam is spit in two beams by a dichroic mirror (16). The 532 nm beam is conducted through a long fibre (17) thus delaying it by e.g. 500 ns and then combined again with the 1064 nm beam in the dichroic mirror (16). The light pulses at 1064 nm and 532 nm appear with 500 ns intervals and are focused to same focal point (22) in the capillary cuvette (23) with lenses (19), (20) and (21a). The set-up is equipped with an appropriate number of photon detectors. For simplicity, only two detectors (28) and (29) are shown in FIG. 6. The emission from the sample is collected by the objective lens (21a) and dichroic mirrors (24) and (25) and lenses (26a) and (26b) through pinholes (27a) and (27b) to detectors (28) and (29) which are connected to an appropriate signal analysis system. In this set-up, the identification signal $D_k$ and the signal F appear at different times, which are separated by the delay time of 500 ns. The signal analysis is synchronized with the pulse laser and the temporal separation eliminates any possible interference between F and $D_k$.

Example 4

Figure 7:
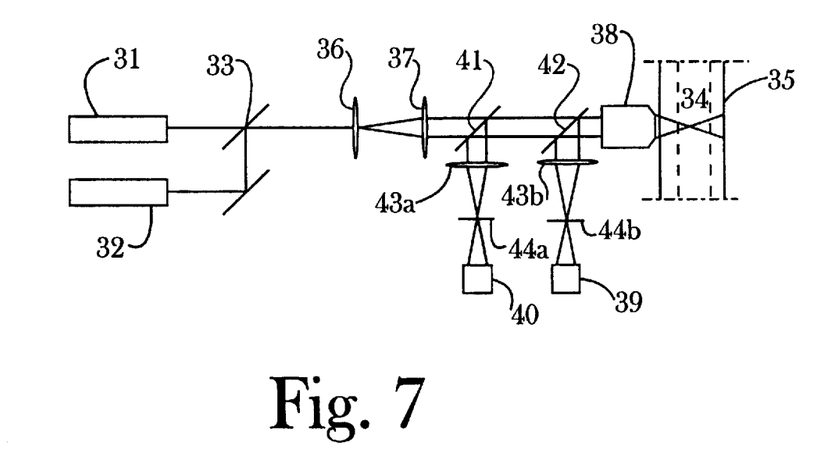
FIG. 7 shows a functional diagram of an alternative measuring system.

In this example we assume the use of e.g. phycoerythrin as fluorescent label and a set of cyanine dyes as identification indicators $D_k$. The idea of this example is to use two photon excitation at 1064 nm for phycoerythrin and single photon excitation at 630 nm for tetrapyrrolic dyes. Referring to FIG. 7 the instrumental set-up applicable for this example comprises a pulsed Q-switched Nd:YAG laser (31) with 1064 nm beam used for excitation of phycoerythrin. The system comprises another laser, e.g. a pulsed diode laser at 630 nm (32). The beams of these lasers are combined using a dichroic mirror (33) and then focused to the same focal point (34) in the capillary cuvette (35) with lenses (36), (37) and (38). The set-up is equipped with an appropriate number of photon detectors. In FIG. 7 only two detectors (39) and (40) are shown for simplicity. The emission from the sample is collected by the objective lens (38), dichroic mirrors (41) and (42) and lenses (43a) and (43b) through pinholes (44a) and (44b) to detectors (40) and (39) which are connected to appropriate signal analysis system. In this set-up, the identification signal $D_k$ and the signal F appear at different times because the pulse lasers are activated at different times respectively. The signal analysis is synchronized with the lasers and the temporal separation eliminates the possible interference between F and $D_k$. The long shift between the emission bands of phycoerythrin and cyanine dyes further enhances the separation.

Example 5

In this example we assume the use of e.g. phycoerythrin as fluorescent label and identification indicators $D_k$ based on Raman scattering. The idea of this example is to use two photon excitation at 1064 nm for phycoerythrin and to detect Raman scattering over the 1100–1200 nm range. Referring to FIG. 6, the instrumental set-up applicable for this example comprises a pulsed or CW Nd:YAG laser (14) producing a 1064 nm beam. (The components 16, 17 and 18 shown in FIG. 6 are not applicable in this Example). The 1064 nm beam is focused to the sample (22) in the capillary cuvette (23) with lenses (19), (20) and (21a). This set-up needs a photon detector (28) for fluorescence emission from label F. The emission from the sample is collected by the objective lens (21a) and dichroic mirrors (25) and lens (26a) through the pinhole (27a) to the detector (28) which are connected to an appropriate signal analysis system. In addition, a detection system for Raman scattering is needed. Raman detection can take place either by a separate 90 degree objective lens (21b) or by the same objective lens (21a) as used for fluorescence. In both cases, Raman scattering will be focused to a pinhole (27b) or (27c) and detected with an appropriate Raman detector (29) or (30). Identification of the microparticle category on the basis of its Raman spectrum can be performed using several alternative and commonly known detection methods. The spectral features specific for microparticles in different categories can be registered with several photon detectors with appropriate spectral filters. Alternatively, registration of the spectrum or its interferogram (the Fourier transform of the frequency spectrum) can be made using e.g. a conventional grating spectrometer or an interferometer, which are coupled to an array detector providing continuous spectrum with adequate resolution. The concentration of the indicators in the microparticle polymer can be high. The intensity of the Nd-YAG-laser is high enough to produce a signal in a short time and strong enough for reliable identification. The identification of the category, i.e. correlation of spectral features, can be performed very fast and simply using known correlation calculation methods.

Example 7

With the reference to FIG. 6 we assume the use of e.g. a coumarin derivative as fluorescent label F and a set of tetrapyrrolic or cyanine dyes as identification indicators $D_k$. The idea of this example is to use two photon excitation at 820 nm for coumarin and single photon excitation at 410 nm for tetrapyrrolic dyes. The instrumental set-up applicable to this example is similar with that used in Example 3, except the laser which in this example is a diode pumped CrLi-Sapphire laser with 80 MHz pulse rate, 30 fs pulse width, 0.5 nJ pulse energy and adjustable 820–900 nm wavelength. The laser is connected to a frequency doubling crystal for the 410 nm line and to a fibre delay line. The high pulse frequency prerequisites lead to shorter delay times and faster single photon counting. In this set-up, the identification signal $D_k$ and the signal F appear at different times which are separated by the delay time. The signal analysis is synchronized with the laser pulses and the temporal separation eliminates any possible interference between F and $D_k$.

Example 8

In this example we assume the use of a polymethinecyanine dye, for example BHDMAP (L. G. Lee & al. Cytometry 21(1995)120–128) as fluorescent label F and a set of tetrapyrrolic dyes as identification indicators $D_k$. The idea of this example is to use two separate lasers and single photon excitation. Referring to FIG. 7, the instrumental set-up applicable for this example comprises a CW frequency doubled Nd:YAG laser (31) with 532 nm beam for $D_k$ and another laser, e.g. a diode laser at 785 nm (32) for excitation of F. Otherwise, the set-up follows the same principles as in Example 4. The long shift between the emission bands of phycoerythrin and the cyanine dye enhances the separation.

A specialist in the field appreciates that the different applications of the said invention may vary within the scope of the claims to be presented in the following section. It will be appreciated that the methods of the present invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

We claim:

1. A biospecific multiparameter assay method based on the use of different categories of microparticles as solid phase representing different analytes to be assayed, each category of microparticles being coated with a different primary biospecific reactant, wherein to said microparticles has been added or the molecular structure of said microparticles contains one or more florescent indicators $D_k$ in one or several concentrations, and the use of secondary biospecific reactants labelled with a photoluminescent label F, said method comprising the steps of pooling the different categories of microparticles together in a suspension and adding the sample containing analytes to be assayed into the suspension, adding a mixture of secondary biospecific reactants labelled with the photoluminescent label F into the suspension to initiate biospecific reactions between the analytes and the labelled reactants and reactants bound to the microparticles, diluting the suspension to reduce the concentration of labelled reactants not bound to the microparticles, activating the indicators $D_k$ and the photoluminescent label F, and measuring the photon emission from the indicators $D_k$ for the identification of the microparticle category and the photon emission from the label F for determination of the analyte concentration, wherein the photoluminescent label F is a short decay time fluorescent label and the excitation and detection of the label F is performed with two-photon excitation and that the susceptibility to two-photon excitation of the fluorescent indicator $D_k$ is substantially lower than that of the photoluminescent label F.

2. The method according to claim 1 wherein the fluorescent indicator $D_k$ comprises a set of fluorescent dyes including one or more of tetrapyrrolic or cyanine compounds wherein said tetrapyrrolic compounds and said cyanine compounds have essentially the same excitation wavelength and separate, narrow and spectrometrically resolvable fluorescence emission bands.

3. The method according to claim 2, wherein said tetrapyrrolic compounds are selected from the group consisting of porphyrin, chlorin, bacteriochlorin, purpurin, pheophorbide, phthalocyanine and naphthalocyanine.

4. The method according to claim 3 wherein the tetrapyrrolic compounds are selected from the group consisting of 1) deuteroporphyrine IX, 2) mesoporphyrine IX, 3) protoporphyrine (IX) dimethyl ester, 4) octaethyl-porphin, 5) tetraphenylporphin, 6) tetra-(2-methoxy)-phenylporphin, 7) chlorin of coproporphyrin dimethyl ester, 8) bacteriochlorin of coproporphyrin dimethyl ester, 9) aluminum phthalocyanine and 10) zinc phthalocyanine.

5. The method according to claim 2 wherein the indicator $D_k$ is a set of fluorescent dyes including at least one cyanine compound selected from the group consisting of 3,3'-diethylthiatricarbocyanine perchlorate;
1,1'-diethyl-2,2,'-dicarbocyanine iodide;
3,3'-diethyloxadicarbocyanine iodide;
3,3'-diethyloxatricarbocyanine iodide;
3,3'-diethylthiadicarbocyanine iodide;
3,3'-diethylthiatricarbocyanine iodide;
IR-125; IR-132; IR-140; and IR-144.

6. The method according to claim 1 wherein the fluorescent indicator $D_k$ comprises a set of fluorescent dyes including one or more of tetrapyrrolic or cyanine compounds, and wherein the photoluminescent label F is phycoerythrin wherein said tetrapyrrolic compounds and said cyanine compounds have essentially the same excitation wavelength and separate; narrow and spectrometrically resolvable fluorescence emission bands.

7. The method according to claim 6, wherein said tetrapyrrolic compounds are selected from the group consisting of porphyrin, chlorin, bacteriochlorin, purpurin, pheophorbide, phthalocyanine and naphthalocyanine.

8. The method according to claim 7, wherein the tetrapyrrolic compounds are selected from the group consisting of 1) deuteroporphyrine IX, 2) mesoporphyrine IX, 3) protoporphyrine (IX) dimethyl ester, 4) octaethyl-porphin, 5) tetraphenylporphin, 6) tetra-(2-methoxy)-phenylporphin, 7) chlorin of coproporphyrin dimethyl ester, 8) bacteriochlorin of coproporphyrin dimethyl ester, 9) aluminum phthalocyanine and 10) zinc phthalocyanine.

9. The method according to claim 6 wherein the indicator $D_k$ is a set of fluorescent dyes including one or more cyanine compounds selected from the group consisting of 3,3'-diethylthiatricarbocyanine perchlorate;
1,1'-diethyl-2,2,'-dicarbocyanine iodide;
3,3'-diethyloxadicarbocyanine iodide;
3,3'-diethyloxatricarbocyanine iodide;
3,3'-diethylthiadicarbocyanine iodide;
3,3'-diethylthiatricarbocyanine iodide;
IR-125; IR-132; IR-140; and IR-144.

10. The method according to claim 1, wherein said photoluminescent label F is a short decay time fluorescent label having a decay time of a few nanoseconds.

11. A biospecific multiparameter assay method based on the use of different categories of microparticles as solid phase representing different analytes to be assayed, each category of microparticles being coated with a different primary biospecific reactant, wherein to said microparticles has been added or the molecular structure of said microparticles contains one or more indicators $D_k$ in one or several concentrations, and the use of secondary biospecific reactants labelled with a photoluminescent label F, said method comprising the steps of pooling the different categories of microparticles together in a suspension and adding the sample containing analytes to be assayed into the suspension, adding a mixture of secondary biospecific reactants labelled with the photoluminescent label F into the suspension to initiate biospecific reactions between the analytes and the labelled reactants and reactants bound to the microparticles, diluting the suspension to reduce the concentration of labelled reactants not bound to the microparticles, activating the indicators $D_k$ and the photoluminescent label F; and measuring the photon emission from the indicators $D_k$ for the identification of the microparticle category and the photon emission from the label F for determination of the analyte concentration wherein the photoluminescent label F is a short decay time fluorescent label and the excitation and detection of the label F is performed either with two-photon excitation or with a confocal optical set-up, and wherein the indicators $D_k$ are compounds added into the microparticle or a molecule structure of the microparticle, said compounds or molecular structure being identifiable on the basis of their Raman spectra.

12. The method according to claim 11, wherein said photoluminescent label F is a short decay time fluorescent label having a decay time of a few seconds.

* * * * *